(12) United States Patent
Moon et al.

(10) Patent No.: US 7,847,092 B2
(45) Date of Patent: Dec. 7, 2010

(54) METHOD FOR PREPARATION OF F-18 CONTAINING ORGANOFLUORO COMPOUNDS IN ALCOHOL SOLVENTS

(75) Inventors: Dae Hyuk Moon, Seoul (KR); Dae Yoon Chi, Seoul (KR); Dong Wook Kim, Incheon (KR); Seung Jun Oh, Seoul (KR); Jin-sook Ryu, Seoul (KR)

(73) Assignees: FutureChem Co., Ltd., Incheon (KR); The Asan Foundation, Seoul (KR)

( * ) Notice: Subject to any disclaimer, the term of this patent is extended or adjusted under 35 U.S.C. 154(b) by 520 days.

(21) Appl. No.: 11/720,393

(22) PCT Filed: Dec. 9, 2005

(86) PCT No.: PCT/KR2005/004228

§ 371 (c)(1),
(2), (4) Date: May 29, 2007

(87) PCT Pub. No.: WO2006/065038

PCT Pub. Date: Jun. 22, 2006

(65) Prior Publication Data

US 2008/0171863 A1 Jul. 17, 2008

(30) Foreign Application Priority Data

Dec. 15, 2004 (KR) .................. 10-2004-0106553
Sep. 10, 2005 (KR) .................. 10-2005-0084411

(51) Int. Cl.
*C07H 19/073* (2006.01)
*C07H 5/02* (2006.01)
*C07D 451/02* (2006.01)
*C07D 233/28* (2006.01)
*C07J 75/00* (2006.01)
*C07C 255/09* (2006.01)
*C07C 19/08* (2006.01)

(52) U.S. Cl. .................. 536/28.54; 536/122; 546/132; 548/327.5; 552/537; 558/427; 570/134

(58) Field of Classification Search .................. None
See application file for complete search history.

(56) References Cited

U.S. PATENT DOCUMENTS 4,985,588 A   1/1991   Kumai et al.

FOREIGN PATENT DOCUMENTS

WO    WO 03/076366    9/2003

OTHER PUBLICATIONS

Schlyer, DJ, Annals Academy of Medicine, PET Tracers and Radiochemistry, (Mar. 2004), vol. 33, issue 2, pp. 146-154.*
Clark, James H., Chemical Review, Fluoride Ion as a Base in Organic Synthesis, (1980), vol. 80, pp. 429-452.*
Free Dictionary "alkyl"; also available at http://www.freedictionary.org/?Query=alkyl; last viewed Jun. 24, 2010.*
Gerstenberger, M.R.C., et al., Chem. Int. De. Engl. 1981, 20, 647-667.
Hoffmann, F.W. J Am. Chem. , Soc. 1948, 70, 2596-2252.
Liotta, C. L., et al., J. Am. Chem. Soc., 1974, 96, 2250-2252.
Cox, D.P., et al., Org. Chem., 1984, 49, 3216-3219.
Kim, D.W., et al., J. Am. Chem. Soc. 2002, 124, 10278-10279.
Kim, D.W., et al. , Nucl. Med. Bio., 2003, 30, 345-350.

* cited by examiner

*Primary Examiner*—Shaojia Anna Jiang
*Assistant Examiner*—Bahar Schmidtmann
(74) *Attorney, Agent, or Firm*—Lucas & Mercanti, LLP

(57) ABSTRACT

The present invention relates to a method for preparation of organofluoro compounds containing radioactive isotope fluorine-18. More particularly, the present invention relates to a method for preparation of primary or secondary organofluoro compound by reacting fluorine salt containing radioactive isotope fluorine-18 with primary or secondary alkyl halide or primary or secondary alkyl sulfonate in the presence of alcohol of Chemical Formula 1 as a solvent to obtain high yield of organofluoro compound. Synthesis reaction according to the present invention may be carried out under mild condition to give high yield of the organofluoro compounds and the reaction time is decreased, and thereby is suitable for the mass production of the organofluoro compounds.

11 Claims, 1 Drawing Sheet

M = alkali metal, alkaline earth metal or alkylammonium
X = $SO_3R^{12}$ or halogen except fluorine

METHOD FOR PREPARATION OF F-18 CONTAINING ORGANOFLUORO COMPOUNDS IN ALCOHOL SOLVENTS

CROSS-REFERENCE TO RELATED APPLICATIONS

This patent application claims the benefit of priority from Korean Patent Application Nos. 10-2004-0106553 filed Dec. 15, 2004, and 10-2005-0084411 filed Sep. 10, 2005, through PCT Application Serial No. PCT/KR2005/004228 filed Dec. 9, 2005, the contents of which are incorporated herein by reference.

TECHNICAL FIELD

The present invention relates to a method for preparation of organofluoro compounds containing fluorine-18, a radioactive isotope of fluorine. More particularly, the present invention relates to a method for preparation of organofluoro compounds to obtain the organofluoro compounds in a high yield by reacting fluorine salt containing radioactive fluorine-18 with alkyl halide or alkyl sulfonate in the presence of alcohol of the Chemical Formula 1 as a solvent.

<Chemical Formula 1>

(wherein $R^1$, $R^2$ and $R^3$ are hydrogen or $C_1$~$C_{18}$ alkyl group)

BACKGROUND ART

Fluorine atom has high polarity and hydrophobic property, and has almost the same size as hydrogen atom. Such organofluoro compounds containing fluorine atoms have unique chemical and physiological properties compared to general organic compounds, and are usefully utilized in the area of medicine, agrochemical, dyestuff, polymer, and the like [Gerstenberger, M. R. C.; Haas, A. Angew. Chem., Int. Ed. Engl. 1981, 20, 647; Filler, R. In Organofluorine Compounds in Medicinal Chemistry and Biomedical Applications; Filler, R., Ed., Studies in Organic Chemistry 48, Elsevier, New York, N.Y., 1993, p 1-23].

Generally organofluoro compounds are prepared from the substitution reaction of fluoride by reacting alkyl halide or alkyl sulfonate with fluorine salt as shown in Chemical Equation 1.

<Chemical Equation 1>

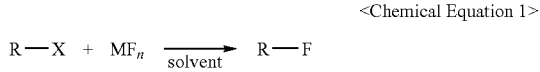

Halide in alkyl halide is selected from the group consisting of Cl, Br, and I except F. Sulfonate in alkyl sulfonate is $SO_3R^{12}$ wherein $R^{12}$ is alkyl or aryl group. The alkyl is preferably $C_1$~$C_{12}$ alkyl halide or $C_1$~$C_{12}$ alkyl sulfonate. For example, the alkyl sulfonate is selected from the group consisting of methane sulfonate, ethane sulfonate, isopropane sulfonate, chloromethane sulfonate, trifluoromethane sulfonate, and chloroethane sulfonate. Aryl group is preferably selected from the group consisting of phenyl, $C_1$~$C_4$ alkyl phenyl, halo phenyl, $C_1$~$C_4$ alkoxy phenyl, and nitro phenyl. Preferable examples are methylphenyl sulfonate, ethylphenyl sulfonate, chlorophenyl sulfonate, bromophenyl sulfonate, methoxylphenyl sulfonate, or nitrophenyl sulfonate.

Fluorine salt (MFn), as a source of fluoride, is selected from the group consisting of alkali metal fluoride containing alkali metals such as lithium, sodium, potassium, rubidium, or cesium; and alkaline earth metal fluoride containing alkaline earth metals such as magnesium, calcium, strontium, or barium; and ammonium fluorides containing ammonium or its derivative such as tetraalkylammonium.

Generally nucleophilic fluorination reaction is carried out in a polar aprotic solvent, such as acetonitrile ($CH_3CN$), DMF, or DMSO, to increase the solubility of fluorine salt and the reactivity of fluoride. It is know that alcohol, a protic solvent, is not suitable for the nucleophilic fluorination reaction. It is further known that alcohol forms hydrogen bonds with fluoride which is a source of fluorine and thereby reduce reactivity in nucleophilic fluorination reaction [Smith, M. D.; March, J. Advanced Organic Chemistry, 5th ed.; Wiley Interscience: New York, N.Y., 2001; pp 389-674].

In the method for preparation of the above organofluoro compounds, it has been reported that alkyl fluoride is prepared by reacting potassium fluoride with alkyl halide in ethylene glycol solvent [Hoffmann, F. W. J. Am. Chem. Soc., 1948, 70, 2596]. However, this preparation method has disadvantages of low yield and long reaction time at high reaction temperature above 140° C., because reactivity is low due to the low solubility of potassium fluoride.

It has been reported that 18-crown-6 ether, which has strong bonds with metal ions, was used as a catalyst to prepare organofluoro compounds to increase the solubility of fluorine salt and the reactivity of fluoride, under relatively low temperature of 80~90° C. and mild reaction conditions, and the yield of the product was high [Liotta, C. L.; Harris, H. P. J. Am. Chem. Soc., 1974, 96, 2250]. However, this process has disadvantages that 18-crown-6 ether is expensive, long reaction time is required and a large amount of alkene is produced as a side product because fluoride acts as base.

It is known that a side reaction, as shown in Chemical Equation 2, is accompanied when fluorine salt is used in the preparation of organofluoro compounds.

<Chemical Equation 2>

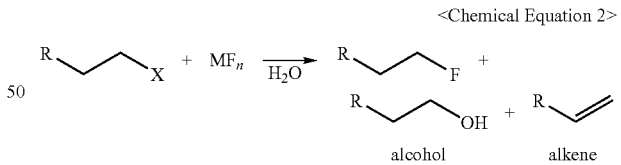

As an example, it is reported that tetrabutylammonium fluoride is used as a fluorine salt to prepare organofluoro compounds in high yield under mild reaction conditions [Cox, D. P.; Terpinsky, J.; Lawrynowicz, W. J. Org. Chem. 1984, 49, 3216.]. However, tetrabutylammonium fluoride hydrate has a problem that a large amount of alcohol, which is a side product caused by water, is produced, and alkene is produced as another side product due to the high basicity of tetrabutylammonium fluoride.

Therefore, for the preparation of organofluoro compounds by the reaction of fluorine salt with alkyl halide or alkyl sulfonate, a preparation method which may reduce the reaction time by increasing the reactivity of fluorine slat, and may reduce the formation of side products such as alkene and alcohol by eliminating the influence of moisture and minimizing basicity of fluoride itself is required.

The inventors have tried to solve the above problems. In the method for preparation of organofluoro compounds by reacting alkyl halide or alkyl sulfonate with fluorine salt, the inventors have found that the present invention is considered to follow the reaction shown in FIG. 1, but is not always limited thereto theoretically. The inventors have found that alcohol solvent increases nucleophilic substitution reactivity of fluorine salt by weakening ionic bonds of fluoride between metal cations and fluorine anions through hydrogen bonds with fluorine metal salts, and side reactions due to the influence of basicity is suppressed in fluorination reaction by weakening the basicity of fluoride through hydrogen bonds of fluoride, and the present invention has been completed.

DISCLOSURE OF INVENTION

Technical Solution

The object of the present invention is to provide a method for preparation of organofluoro compounds with high yield through the reaction of fluorine salt with alkyl halide or alkyl sulfonate by increasing the solubility of fluorine salt through weakened ionic bonds of fluoride between metal cations and fluorine anions, and by shorting reaction time at the same time through increased reactivity of the fluoride. The method for preparation may increase the nucleophilic substitution reactivity of fluorine salt and reduce the formation of side products at the same time by eliminating the influence of moisture or reducing basicity of fluoride itself.

Advantageous Effects

According to the present invention, the organofluoro compounds as major products may be selectively prepared in the yield above 90% by suppressing the formation of the side reactions with the use of alcohol as reaction solvent. The alcohol solvent increases nucleophilic substitution reactivity of the fluorine salt by weakening the ionic bonds between metal cations and fluorine anions through the formation of hydrogen bonds with fluorine metal salts, thereby the problem of the low reactivity due to the strong ionic bond of fluorine in a conventional method may be overcome, reaction time may be shortened by increased reactivity and reaction rate of the fluorine salt, and the formation of side products due to the influence of basicity may be suppressed by weakening the basicity of the fluoride through the hydrogen bond of the fluoride.

BEST MODE FOR CARRYING OUT THE INVENTION

The present invention provides a method for preparation of organofluoro compounds by using alcohol of Chemical Formula 1 as a solvent, wherein the organofluoro compounds are prepared by reacting fluorine salt with alkyl halide or alkyl sulfonate.

<Chemical Formula 1>

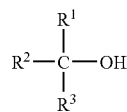

(wherein $R^1$, $R^2$ and $R^3$ are hydrogen or $C_1 \sim C_{18}$ alkyl group)

Organofluoro compounds in the present invention are organofluoro compounds containing fluorine-18 and/or fluorine-19.

Preferably $R^1$ is hydrogen or $C_1 \sim C_{18}$ alkyl group, preferably $R^2$ is hydrogen or $C_1 \sim C_{18}$ alkyl group, preferably $R^3$ is hydrogen or $C_1 \sim C_{18}$ alkyl group $R^3$ more preferably $R^1$ is methyl or ethyl, more preferably $R^2$ is methyl or ethyl, more preferably $R^3$ is methyl or ethyl in the method for preparation of organofluoro compounds in accordance with the present invention.

Figure 1:
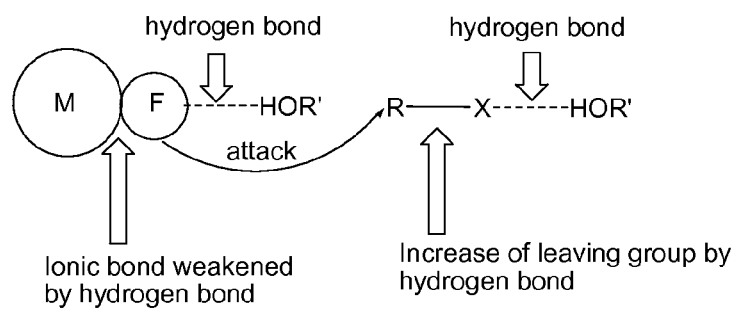
FIG. 1 is a diagram showing the concept that alcohol weakens ionic bonds between metal cations and fluorine anions through the formation of hydrogen bond with fluorine metal salt in accordance with an example embodiment of the present invention.

The alcohol of Chemistry FIG. 1 is preferably selected from the group consisting of primary alcohols such as methanol, ethanol, n-propanol, n-butanol, amyl alcohol, n-hexyl alcohol, n-heptanol, or n-octanol; secondary alcohols such as isopropanol, isobutanol, isoamyl alcohol, 3-pentanol; and tertiary alcohols such as t-butanol, t-amyl alcohol, 2,3-dimethyl-2-butanol, 2-(trifluoromethyl)-2-propanol, 3-methyl-3-pentanol, 3-ethyl-3-pentanol, 2-methyl-2-pentanol, 2,3-dimethyl-3-pentanol, 2,4-dimethyl-2-pentanol, 2-methyl-2-hexanol, 2-cyclopropyl-2-propanol, 2-cyclopropyl-2-butanol, 2-cyclopropyl-3-methyl-2-butanol, 1-methylcyclopentanol, 1-ethylcyclopentanol, 1-propylcyclopentanol, 1-methylcyclohexanol, 1-ethylcyclohexanol, and 1-methylcycloheptanol. More preferably the alcohol is selected from the group consisting of tertiary alcohols such as t-butanol, t-amyl alcohol, 2,3-dimethyl-2-butanol and 2-(trifluoromethyl)-2-propanol in the method for preparation of organofluoro compounds in accordance with the present invention.

The fluoride salt is preferably selected from the group consisting of alkali metal fluorides containing alkali metals selected from the group consisting of lithium, sodium, potassium, rubidium, and cesium; alkaline earth metal fluorides containing alkaline earth metals selected from the group consisting of magnesium, calcium, strontium, and barium; and ammonium fluoride. More preferably cesium fluoride and ammonium fluoride is desirable in the method for preparation of organofluoro compounds in accordance with the present invention.

The above ammonium fluoride is preferably selected from the group consisting of quaternary ammonium fluorides including tetrabutylammonium fluoride and benzyltrimethylammonium fluoride; tertiary ammonium fluorides including triethylammonium fluoride and tributylammonium fluoride; secondary ammonium fluorides including dibutylammonium fluoride and dihexylammonium fluoride; and primary ammonium fluorides including butylammonium fluoride and hexylammonium fluoride, more preferably tetrabutylammonium fluoride is desirable in the method for preparation of organofluoro compounds in accordance with the present invention.

Tetraalkylammonium fluoride or alkali metal fluoride including cesium is preferably adsorbed by supports selected from the group consisting of Celite, Molecular Sieve, alumina, and silica gel in the method for preparation of organofluoro compounds in accordance with the present invention.

For the most preferable combination of fluorine salt and alcohol, the fluorine salt is metal fluoride or tetraalkylammonium fluoride, more specifically cesium fluoride or tetrabutylammonium fluoride, and the preferable alcohol is tertiary alcohol such as t-butanol and t-amyl alcohol in the method for preparation of organofluoro compounds in accordance with the present invention.

The amount of the above fluorine salt is preferably 1.0~10 equivalents for alkyl halide or alkyl sulfonate in the method for preparation of organofluoro compounds in accordance with the present invention.

Organofluoro compounds prepared by using alcohol of Chemical Formula 1 as solvent is [$^{18}$F]fluorodeoxyglucose of Chemical Formula 2 in the method for preparation of organofluoro compounds in accordance with the present invention.

<Chemical Formula 2>

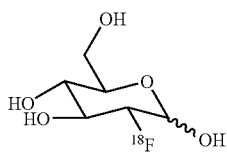

<Chemical Formula 2>

Organofluoro compounds prepared by using alcohol of Chemical Formula 1 as solvent is [$^{18}$F]fluoromisonidazole of Chemical Formula 3 in the method for preparation of organofluoro compounds in accordance with the present invention.

<Chemical Formula 3>

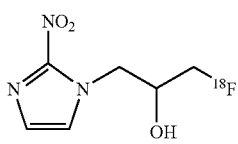

<Chemical Formula 3>

Organofluoro compounds prepared by using alcohol of Chemical Formula 1 as solvent is [$^{18}$F]fluoroestradiol of Chemical Formula 4 in the method for preparation of organofluoro compounds in accordance with the present invention.

<Chemical Formula 4>

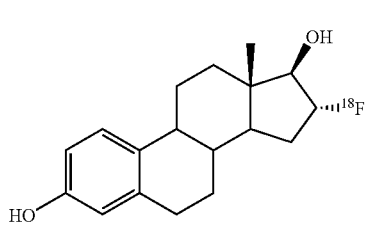

<Chemical Formula 4>

Organofluoro compounds prepared by using alcohol of Chemical Formula 1 as solvent is [$^{18}$F]fluoropropylcarbomethoxytropane of Chemical Formula 5 in the method for preparation of organofluoro compounds in accordance with the present invention.

<Chemical Formula 5>

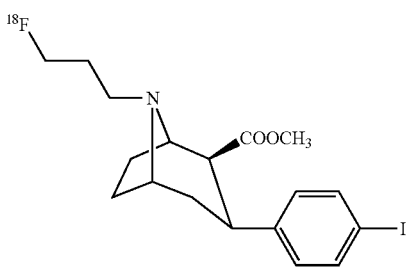

<Chemical Formula 5>

Organofluoro compounds prepared by using alcohol of Chemical Formula 1 as solvent is [$^{18}$F]fluoroDDNP of Chemical Formula 6 in the method for preparation of organofluoro compounds in accordance with the present invention.

<Chemical Formula 6>

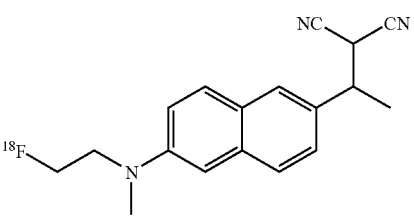

<Chemical Formula 6>

Organofluoro compounds prepared by using alcohol of Chemical Formula 1 as solvent is [$^{18}$F]fluorothymidine of Chemical Formula 7 in the method for preparation of organofluoro compounds in accordance with the present invention.

<Chemical Formula 7>

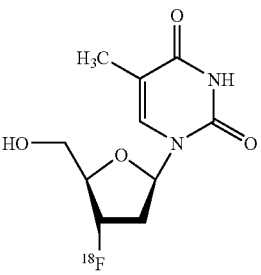

<Chemical Formula 7>

Organofluoro compounds prepared by using alcohol of Chemical Formula 1 as solvent is [$^{18}$F]fluorocholine of Chemical Formula 8 in the method for preparation of organofluoro compounds in accordance with the present invention.

<Chemical Formula 8>

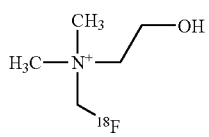

<Chemical Formula 8>

Organofluoro compounds prepared by using alcohol of Chemical Formula 1 as solvent is [$^{18}$F]fluoroethylcholine of Chemical Formula 9 in the method for preparation of organofluoro compounds in accordance with the present invention.

<Chemical Formula 9>

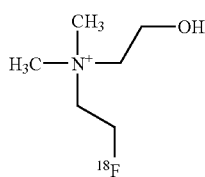

<Chemical Formula 9>

Organofluoro compounds prepared by using alcohol of Chemical Formula 1 as solvent is [$^{18}$F]fluoropropylcholine of Chemical Formula 10 in the method for preparation of organofluoro compounds in accordance with the present invention.

<Chemical Formula 10>

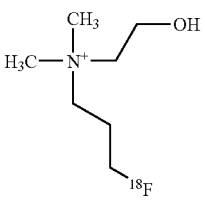

<Chemical Formula 10>

In the preparation method according to the present invention, the alcohol solvent forms hydrogen bond with fluoride and thereby increases nucleophilic substitution reaction of fluorine salt. Thus the problem of low fluoride reactivity due to theionic bonds of fluoride between metal cations and fluorine anions may be overcome, reaction time may be reduced and the final product of organofluoro compound may be obtained in high yield by suppressing the side reaction at the same time.

MODE FOR THE INVENTION

Hereinafter, example embodiments of the present invention will be described in more detail.

In a method for preparation of organofluoro compound through the reaction of fluorine salt with alkyl halide or alkyl sulfonate, alcohol of Chemical Formula 1 is used as solvent. Preferably the reaction is carried out at 0~150° C. for 0.5~24 hrs, more preferably the reaction is carried out for 1~10 hrs at 20~120° C., further more preferably the reaction is carried out at 40~100° C. for 1.5~6 hrs.

Boiling point, affinity to water, chemical stability and reactivity of alcohol depend on the composition of alkyl group in the alcohol of Chemical Formula 1.

As the number of carbon in alkyl group of alcohol and alkyl substituent increases, boiling and melting point of alcohol become high. Alcohol having the high boiling point and melting point is not suitable for solvent or exists in a solid state. Alcohol having a low number of carbon in alkyl group or a less alkyl substituents is not suitable for solvent because the reactivity of alcohol itself is increased due to decrease of steric hindrance of alcohol.

Considering these effects, $R^1$ is preferably hydrogen or $C_1$~$C_{18}$ alkyl, more preferably $C_1$~$C_6$ alkyl, further more preferably methyl or ethyl.

$R^2$ is preferably hydrogen or $C_1$~$C_{18}$ alkyl, more preferably $C_1$~$C_6$ alkyl, further more preferably methyl or ethyl.

$R_3$ is preferably hydrogen or $C_1$~$C_{18}$ alkyl, more preferably $C_1$~$C_6$ alkyl, further more preferably methyl or ethyl.

As examples of alcohol described in the above, preferably alcohol is selected from the group consisting of primary alcohols such as methanol, ethanol, n-propanol, n-butanol, amyl alcohol, n-hexyl alcohol, n-heptanol and n-octanol; and secondary alcohols such as isopropanol, isobutanol, isoamyl alcohol and 3-pentanol; and tertiary alcohols such as t-butanol, t-amyl alcohol, 2,3-dimethyl-2-butanol, 2-(trifluoromethyl)-2-propanol, 3-methyl-3-pentanol, 3-ethyl-3-pentanol, 2-methyl-2-pentanol, 2,3-dimethyl-3-pentanol, 2,4-dimethyl-2-pentanol, 2-methyl-2-hexanol, 2-cyclopropyl-2-propanol, 2-cyclopropyl-2-butanol, 2-cyclopropyl-3-methyl-2-butanol, 1-methylcyclopentanol, 1-ethylcyclopentanol, 1-propylcyclopentanol, 1-methylcyclohexanol, 1-ethylcyclohexanol and 1-methylcycloheptanol. More preferably the alcohol is selected from the group consisting of the tertiary alcohols such as t-butanol, t-amyl alcohol, 2,3-dimethyl-2-butanol and 2-(trifluoromethyl)-2-propanol.

The alcohol solvent according to the present invention increases nucleophilic substitution reactivity of the fluorine salt by weakening the ionic bonds of fluoride between metal cations and fluorine anions through the formation of hydrogen bond with metal fluoride and tetraalkylammonium fluoride, and also suppresses the formation of side reaction by weakening the basicity of fluoride.

The method according to present invention is considered to follow the reaction scheme schematically shown in FIG. 1, but is not always limited thereto theoretically. Additionally it has been found that the reaction of alkyl sulfonate is more effective than that of alkyl halide because alcohol forms hydrogen bond with alkyl sulfonate.

The fluorine salt supplying fluoride ion may be selected from the group consisting of alkali metal fluorides containing alkali metals selected from the group consisting of lithium, sodium, potassium, rubidium, and cesium; and alkaline earth metal fluorides containing alkali earth metals selected from the group consisting of magnesium, calcium, strontium, and barium; and ammonium fluoride, in the preparation of organofluoro compounds in accordance with the present invention.

The above ammonium fluoride may be selected from the group consisting of quaternary ammonium fluorides such as tetrabutylammonium fluoride and benzyltrimethylammonium fluoride; and tertiary ammonium fluorides such as triethylammonium fluoride and tributylammonium fluoride; secondary ammonium fluorides such as dibutylammonium fluoride and dihexylammonium fluoride; and primary ammonium fluorides such as butylammonium fluoride and hexylammonium fluoride, most preferably cesium fluoride or tetrabutyl ammonium fluoride may be used.

Alkali metal fluoride including cesium and tetraalkyl ammonium fluoride may be used in forms absorbed to various supports. For example, cesium fluoride and tetrabutylammonium fluoride adsorbed to supports such as Celite, Molecular Sieve, alumina, and silica gel may be used. When fluorine-19 is used, the amount of fluorine salt is preferably 1.0~10 equivalents for alkyl halide or alkyl sulfonate, more preferably 3.0~6.0 equivalents. When the fluorine salt is added less than the above range, the yield is low. When the fluorine salt is added more than the above range, the yield is high but it is waste of fluorine salt.

By the same reason, in the case of fluorine-18, trace amount of [$^{18}$F]fluoride is preferably used as the fluorine salt compared to the amount of alkyl halide or alkyl sulfonate. More preferably, 1 pg~100 ng of [$^{18}$F]fluoride for 1 mg of the alkyl halide or alkyl sulfonate is used.

In the other hand, organofluoro compound labeled with fluorine-18 may be prepared by reacting alkyl halide or alkyl sulfonate with fluorine salt of positron emitting radioactive isotope fluorine-18. Here, fluorine of the fluorine salt, which is a radioactive isotope, is a fluorine-18, specifically [$^{18}$F]fluoride.

In the method for preparation of the organofluoro compound by the reaction of fluorine salt with alkyl halide or alkyl sulfonate, the organofluoro compound as a major product is selectively prepared in high yield above 90% by suppressing the side reaction with the use of tertiary alcohol as a reaction solvent.

On the contrary, in accordance with an embodiment of the present invention, in the case of acetonitrile or DMF, which are polar aprotic solvents conventionally used to prepare organofluoro compounds, yield is low due to the low solubility of fluorine salt. When reaction is carried out by using 1,4-dioxane or benzene which are non-polar solvent, the organofluoro compound is not prepared at all (refer to Table 1).

In conclusion, the alcohol solvent used in the present invention increases nucleophilic substitution reactivity of fluorine salt by weakening the ionic bonds between metal cations and fluorine anions through the formation of hydrogen bond with alkali metal fluoride and tetraalkylammonium fluoride, thus the problem of low fluoride reactivity due to the strong ionic bond of fluorine salt in a conventional method may be overcome, the reaction time is shortened by increasing reactivity and reaction rate of the fluorine salt, and organofluoro compound according to the present invention is obtained in high yield.

In addition, alcohol, a protic solvent, may suppress the formation of side products due to the influence of basicity during fluorination reaction by weakening the basicity of the fluoride through the formation of hydrogen bond with the fluoride. Therefore, the formation of side products such as alcohols and alkenes may be reduced.

According to the present invention, the method for preparation of organofluoro compounds using alcohol of Chemical Formula 1 as a solvent may prepare organofluoro compounds in higher yield, at shorter reaction time, and under the milder reaction condition than the conventional preparation method. Another preparation method already disclosed by the inventors shows that organofluoro compounds may be prepared in high yield (Kim, D. W.; Song, C. E.; Chi, D. Y. *J. Am. Chem. Soc.*, 2002, 124, 10278-10279). However the method described in the above paper has an economical disadvantage because expensive ionic liquid is required while inexpensive alcohols are used in the present invention.

The above conventional method is very useful for the preparation of nonpolar organofluoro compounds. For example, $^{18}$F labeled organofluoro compounds may be prepared in high yield (Kim, D. W.; Choe, Y. S.; Chi, D. Y. *Nucl. Med. Biol.* 2003, 30, 345-350). When $^{18}$F labeled radioactive medicines are actually synthesized, this method has a disadvantage that separation from ionic liquid is very difficult because most of $^{18}$F labeled radioactive medicines are polar. Therefore, the above method may not be usefully utilized in the preparation of $^{18}$F labeled radioactive medicines.

In this regard, the present invention has a significant applicability in the preparation of the $^{18}$F labeled radioactive medicines. The present invention provides various applications for the preparation of $^{18}$F labeled radioactive medicines. Example embodiments according to the present invention are intended for the applications to existing $^{18}$F labeled radioactive medicines.

The present invention will be illustrated in more detail with the reference to the following examples. The following embodiments are examples of the present invention, and the present invention should not be construed as being limited to the embodiments set forth herein; rather, these embodiments are provided to fully convey the concept of the invention to those skilled in the art. It will be understood by those skilled in the art that various changes in form and details may be made thereto without departing from the spirit and scope of the invention as defined by the appended claims.

Example 1

Preparation of Organofluoro Compound 1

280 mg (1.0 mmol) of 2-(3-methanesulfonyloxypropoxy) naphthalene and 456 mg (3.0 mmol) of cesium fluoride are added to a solvent of 4.0 mL of t-butanol. The reaction mixture is stirred for 6 hrs at 80° C. 7 mL of ethyl ether is added to the reaction mixture to remove metal salts. After filtration, the filtrate is concentrated by reduced pressure distiller. 188 mg (92% yield) of 2-(3-fluoropropoxy)naphthalene is obtained by column chromatography (ethyl acetate:n-hexane=1:20).

Example 2

Preparation of Organofluoro Compounds 2~7

The reactions are carried out by the same method as described in Example 1 except that kinds of alcohol solvent, reaction temperature and time are same as described in the Table 1. Organofluoro compounds are prepared as shown in the Table 1. Chemical Equation 3 shows 2-(3-fluoropropoxy) naphthalene (A), 2-(3-hydroxypropoxy)naphthalene (B), 2-(3-allyloxy)naphthalene (C) and 2-(3-alkoxypropoxy) naphthalene (D), which are the products obtained in the preparation of the organofluoro compounds.

Comparative Example 1

Preparation of Organofluoro Compound 1

280 mg (1.0 mmol) of 2-(3-methanesulfonyloxypropoxy) naphthalene and 456 mg (3.0 mmol) of cesium fluoride are added to 4.0 mL of acetonitrile instead of alcohol solvent. The reaction mixture is stirred for 6 hrs at 80° C.

The reaction does almost not proceed and it is identified that the role of alcohol solvent is essential for the preparation of organofluoro compounds.

Comparative Example 2

Preparation of Organofluoro Compound 2

280 mg (1.0 mmol) of 2-(3-methanesulfonyloxypropoxy) naphthalene and 456 mg (3.0 mmol) of cesium fluoride are added to 4.0 mL of DMF instead of alcohol solvent. The reaction mixture is stirred for 6 hrs at 80° C.

33% of reactants still exist after the reaction. Considerable amount of alcohol and alkene side products are formed. It is identified that the role of alcohol solvent is essential for the preparation of organofluoro compounds.

Comparative Examples 3~4

Preparation of Organofluoro Compounds 3~4

280 mg (1.0 mmol) of 2-(3-methanesulfonyloxypropoxy) naphthalene, 456 mg (3.0 mmol) of cesium fluoride are added to 4.0 mL of benzene or 1,4-dioxane instead of alcohol. The reaction mixture is stirred for 6 hrs at 80° C.

The reaction does almost not proceed and it is identified that the role of alcohol solvent is essential for the preparation of organofluoro compounds.

Comparative Examples 5~6

Preparation of Organofluoro Compounds 5~6

To confirm the increase of the reactivity due to hydrogen bond between fluorine salt and alcohol solvent, the reaction is carried out in the same method as the Example 1 by using potassium bromide, which does not form hydrogen bond with alcohol, instead of fluorine salt.

Bromination reaction does almost not proceed, and it is identified that the hydrogen bond between alcohol solvent and fluorine salt is essential to increase the reactivity of fluorine salt.

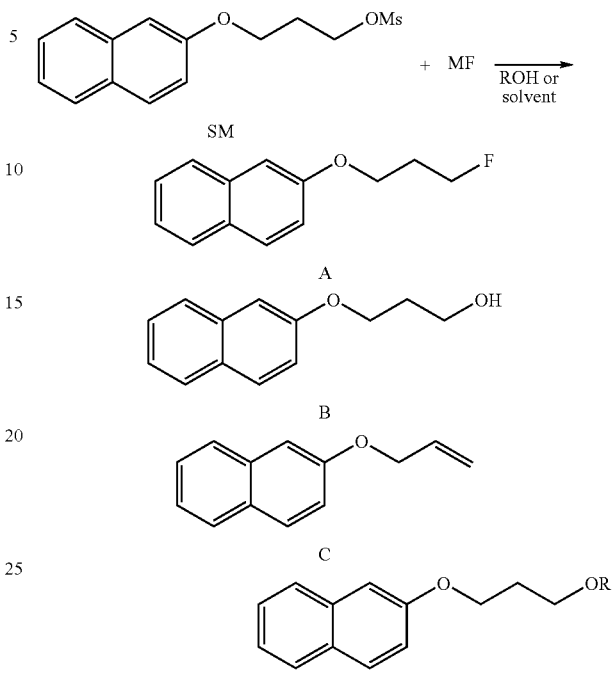

<Chemical Equation 3>

The data in Table 1 show that 2-(3-fluoropropoxy)naphthalene (A) is prepared (92% yield) when cesium fluoride is used as fluoride source, and tertiary alcohols of t-butanol or t-amyl alcohol are used as solvent (Examples 1, 3, and 4).

When tetrabutylammonium fluoride is used as fluorine source instead of cesium fluoride, the yield of the major product is above 90% (Example 7). When rubidium fluoride is used, fluorination reaction proceeds, but long reaction time is required (Example 5).

TABLE 1

| | solvent | fluorine salt | temperature (° C.) | time (h) | yield | | | | |
|---|---|---|---|---|---|---|---|---|---|
| | | | | | SM | A | B | C | D |
| Example 1 | t-BuOH | CsF | 80 | 6 | trace | 92 | — | — | 7 |
| Example 2 | n-BuOH | CsF | 80 | 6 | 4 | 64 | — | — | 30 |
| Comparative Example 1 | $CH_3CN$ | CsF | 80 | 6 | 91 | 7 | — | trace | — |
| Comparative Example 2 | DMF | CsF | 80 | 6 | 33 | 48 | 8 | 9 | — |
| Comparative Example 3 | 1,4-dioxane | CsF | 80 | 6 | 94 | — | — | — | — |
| Comparative Example 4 | benzene | CsF | 80 | 6 | 97 | — | — | — | — |
| Example 3 | t-amyl alcohol | CsF | 80 | 6 | — | 93 | — | — | 5 |
| Example 4 | t-amyl alcohol | CsF | 80 | 2.5 | — | 94 | — | — | 4 |
| Comparative Example 5 | t-amyl alcohol | KBr | 80 | 6 | 94 | trace | — | — | — |
| Comparative Example 6 | $CH_3CN$ | KBr | 80 | 6 | 67 | 30 | — | — | — |
| Example 5 | t-amyl alcohol | RbF | 80 | 24 | 13 | 76 | — | — | 9 |
| Example 6 | t-amyl alcohol | KF | 80 | 24 | 90 | trace | — | — | 7 |
| Example 7 | t-amyl alcohol | TBAF | 80 | 1 | — | 92 | trace | — | 4 |

In the case of the Comparative Examples 1 and 2 using polar aprotic solvent, which is conventionally used for the preparation of organofluoro compounds, and in the case of nonpolar solvent, the reaction mixture is treated for 6 hrs. The reaction does not occur at all or large amounts of side products are formed and the yield of the product is only 48%. This result shows that the use of alcohol is essential for the production of organofluoro compounds. 2-(3-n-butoxypropoxy) naphthalene (D), a side product of ether, is formed (30%) when n-butanol, a primary alcohol, is used as solvent. This result shows that the use of tertiary alcohol instead of primary or secondary alcohols suppresses the production of ether compounds as side product.

In the Comparative Examples 5 and 6, potassium bromide incapable of forming hydrogen bonds is used instead of fluorine salt to confirm the increase of reactivity due to hydrogen bonds between alcohol solvent and fluorine salt. It is identified that bromination reaction does almost not proceed, and the hydrogen bond between alcohol solvent and fluorine salt is essential to increase the reactivity of fluorine salt in the preparation of organofluoro compounds.

Example 8

Preparation of Organofluoro Compound 8

356 mg (1.0 mmol) of 2-(3-toluenesulfonyloxypropoxy) naphthalene and 456 mg (3.0 mmol) of cesium fluoride are added to 4.0 mL of t-amyl alcohol in a reaction vessel. The reaction mixture is stirred for 2 hrs at 90° C. 7 mL of ethyl ether is added to remove metal salt. After filtration, the filtrate is concentrated by a reduced pressure distiller. 190 mg (93% yield) of 2-(3-fluoropropoxy)naphthalene is obtained by column chromatography (ethyl acetate:n-hexane=1:20).

Examples 9-14

Preparation of Organofluoro Compounds 9-14

The reactions are carried out by the same method as described in Example 8 except that 1.0 mmol of several alkyl halides or alkyl sulfonates shown in the table 2 are used instead of 2-(3-toluenesulfonyloxypropoxy)naphthalene.

TABLE 2

| | Alkyl halide or Alkyl sulfonate | temperature (° C.) | time (h) | yield (%) |
|---|---|---|---|---|
| Example 8 | naphthalene-O-CH₂CH₂CH₂-OTs | 90 | 2 | 93 |
| Example 9 | naphthalene-O-CH₂CH₂CH₂-I | 90 | 24 | 73 |
| Example 10 | naphthalene-O-CH₂CH₂-I | reflux | 12 | 72 |
| Example 11 | naphthalene-O-CH₂CH₂CH₂-Br | reflux | 18 | 88 |
| Example 12 | naphthalene-O-CH₂-CH(CH₃)-OMs | 90 | 3.5 | 81 |
| Example 13 | naphthalene-CH₂CH₂-OMs | 90 | 2.5 | 92 |
| Example 14 | (2S,4R)-N-Boc-4-OTf-proline methyl ester | 25 | 1.5 | 69 |

Example 15

Preparation of Organofluoro Compound 15

Preparation of [$^{18}$F]fluorodeoxyglucose (FDG)

The preparation process of [$^{18}$F]fluorodeoxyglucose is shown in Chemical Equation 4. 10 mCi of [$^{18}$F]fluoride is adsorbed on ion exchange resin. The adsorbed [$^{18}$F]fluoride is eluted to a reaction vessel by the mixture solution of cesium carbonate (16 mg in 300 μL water) and Kryptofix 222 (22 mg in 300 μL acetonitrile) or tetrabuty-lammonium solution. The [$^{18}$F]fluoride is dried by acetonitrile solvent (500 μL×3). To the solution 20 mg mannose triflate is added. And then the mixture solution containing 300 μL t-butyl alcohol or t-amyl alcohol and 300 μL acetonitrile is added to the reaction mixture. The reaction is carried out at 100° C. for 15 min. The solvent is removed at 95° C. using nitrogen gas and then 500 μL of 2N NaOH solution is added. The hydrolysis reaction is carried out for 2 minutes at room temperature and then 3 mL of water is added for dilution. The reaction mixture is sequentially passed through neutral alumina cartridge, tC18 cartridge, and IC-H$^+$ cartridge to obtain pure [$^{18}$F]fluorodeoxy glucose. In the experiment carried out under the above reaction condition, the attenuation-corrected radiochemical yield is 95.1+2.7% and the radiochemical purity is 98.2+1.3%.

<Chemical Equation 4>

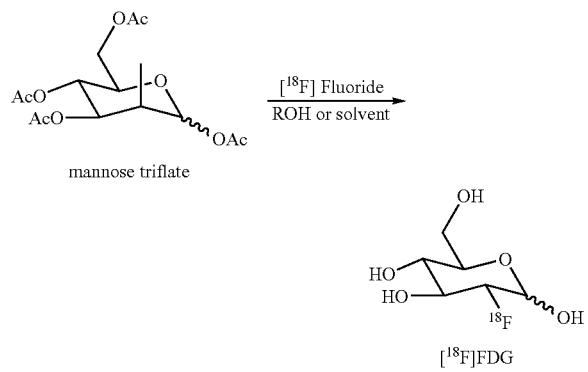

Example 16

Preparation of Organofluoro Compound 16

Automatic Preparation of [$^{18}$F]fluorodeoxyglucose (FDG)

Figure 2:
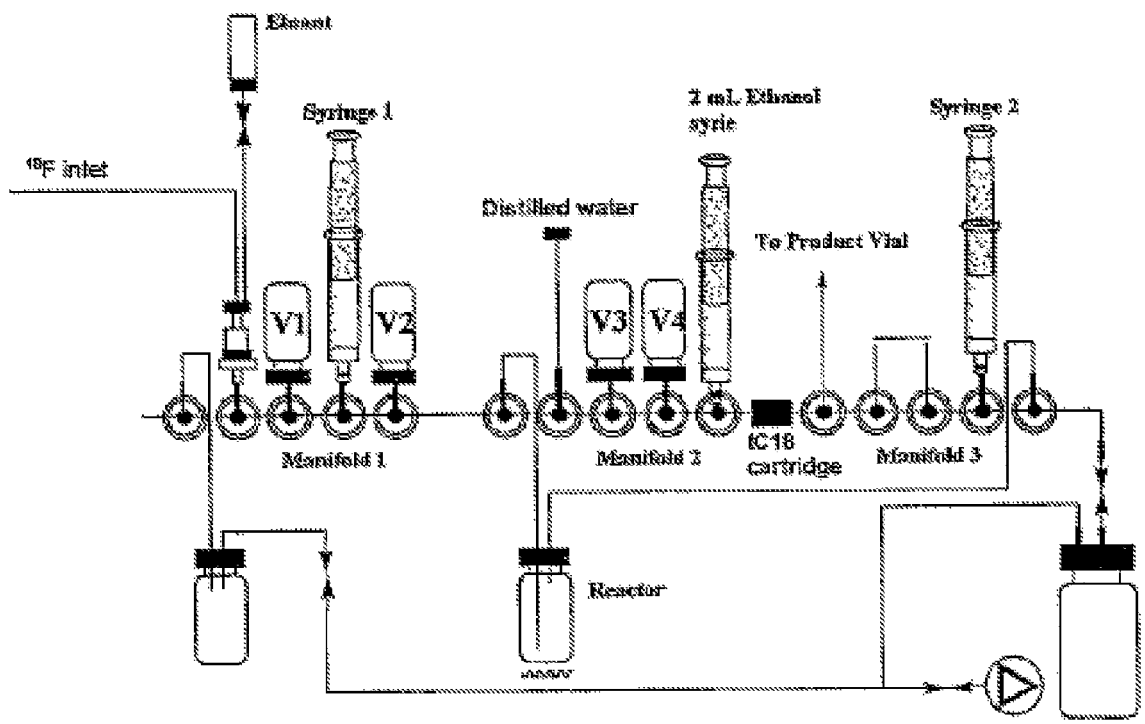
FIG. 2 is a schematic diagram of disposable cassette in accordance with an example embodiment of the present invention.

Automatic preparation of [$^{18}$F]fluorodeoxyglucose is carried out according to the reaction condition described in Example 15. The apparatus for the automatic preparation is GE TracerLab MX, and the operation program is modified for the preparation of [$^{18}$F]fluorodeoxyglucose. A disposable cassette is used for the preparation and the schematic diagram of the cassette is shown in FIG. 2.

After a disposable cartridge for the GE TracerLab MX is installed in the automatic equipment, chemicals are added as follows; 7 mL acetonitrile in 10 mL V1 vial, 20 mg mannose triflate (1.2 mL t-butyl alcohol or t-amyl alcohol and 0.8 mL acetonitrile) in 10 mL V2 vial, 5 mL ethanol in 10 mL V3 vial, 5 mL 1 N HCl solution and buffer solution in V4 vial, and 2 mL 2 N NaOH solution in 2 mL syringe.

1,000 mCi [$^{18}$F]fluoride is prepared from oxygen-18 labeled water in a cyclotron and then the [$^{18}$F]fluoride is transferred to the GE TracerLab MX automatic equipment by the pressure of helium gas. The transferred [$^{18}$F]fluoride is adsorbed on the ion exchange resin cartridge and oxygen-18 is recovered to an oxygen-18 water reservoir. The adsorbed [$^{18}$F]fluoride is eluted to the reaction vessel by the mixture solution of cesium carbonate (16 mg in 300 □water) and Kryptofix 222 (22 mg in 300 □acetonitrile) or by tetrabutylammonium solution. The eluted [$^{18}$F]fluoride is completely dried by 1 mL acetonitrile in V1 vial. After the addition of mannose triflate in V2 vial to the reaction vessel containing the dried [$^{18}$F]fluoride, the reaction is carried out at 100° C. for 15 min. and then the solvent is completely removed. 1 mL acetonitrile in V1 vial is added to the reaction vessel, and then the mixture is transferred to the syringe 1 in FIG. 2. The reaction intermediate is diluted by the addition of 25 mL water and then adsorbed on tC18 cartridge. After the addition of 2 N NaOH solution in a 2 mL syringe to the adsorbed intermediate for the hydrolysis, pure [$^{18}$F]fluorodeoxyglucose is obtained after purification by passing through neutral alumina cartridge and tC18 cartridge. When the automatic preparation is carried out under the above condition, the attenuation-corrected radiochemical yield is 75.1±7.4% and the radiochemical purity is 98.2±1.2%.

Example 17

Preparation of Organofluoro Compound 17

Preparation of [$^{18}$F]fluoromisonidazole (FMISO) 1

The preparation process of [$^{18}$F]fluoromisonidazole is shown in Chemical Equation 5. 10 mCi [$^{18}$F]fluoride is adsorbed on ion exchange resin. The adsorbed [$^{18}$F]fluoride is eluted to a reaction vessel by the mixture solution of cesium carbonate (2 mg in 300 μL water) and Kryptofix 222 (22 mg in 300 μL acetonitrile) or by tetrabutylammonium solution. The [$^{18}$F]fluoride is dried by acetonitrile (500 μL×3). To this solution 10 mg 1-(1,2-epoxypropyl)-2-nitroimidazole is added. After the addition of the mixture solution containing 500 μL t-butyl alcohol or t-amyl alcohol and 100 μL acetonitrile to the above reaction mixture, the reaction is carried out at 100° C. for 15 min. The solvent is removed using nitrogen gas at 95° C., and then 200 μL acetonitrile and 1000 μL water are added to the reaction vessel. Pure [$^{18}$F]fluoromisonidasole is obtained by high pressure liquid chromatography (HPLC). The condition of HPLC is as follows;

Alltech Econosil C18 column is used, a mixture solution of water:ethanol=95:5 is used at the flow rate of 5 mL/min., And the equipment has a 254 nm UV detector and radioactive detector. In the experiment carried out under the above reaction condition, the attenuation-corrected radiochemical yield is 75.4±3.1% and the radiochemical purity is 98.1±0.7%.

<Chemical Equation 5>

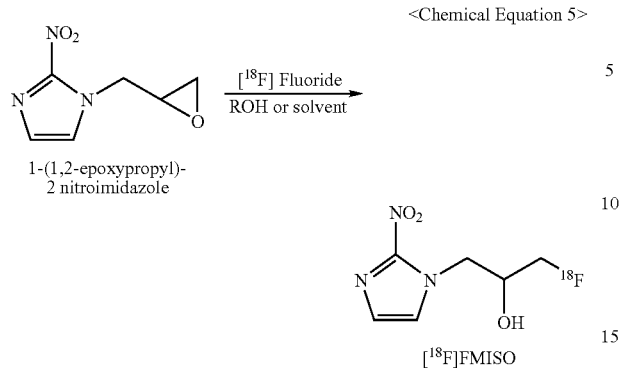

1-(1,2-epoxypropyl)-
2 nitroimidazole

[$^{18}$F]FMISO

Example 18

Preparation of Organofluoro Compound 18

Preparation of [$^{18}$F]fluoromisonidazole (FMISO) 2

Another preparation process of [$^{18}$F]fluoromisonidazole is shown in the Chemical Equation 6. 10 mCi of [$^{18}$F]fluoride is adsorbed on ion exchange resin. The adsorbed [$^{18}$F]fluoride is eluted to a reaction vessel by the mixture solution of cesium carbonate (16 mg in 300 μL water) and Kryptofix 222 (22 mg in 300 μL acetonitrile) or tetrabuty-lammonium solution. The [$^{18}$F]fluoride is dried by acetonitrile (500 μL×3). To this solution 10 mg 1-(2-nitro-1-imidazoyl)-2-O-tetrahydropyranyl-3-O-toluenesulfonyloxypropandiol is added. After the addition of the mixture solution containing 500 μL t-butyl alcohol or t-amyl alcohol and 100 μL acetonitrile to the above reaction mixture, the reaction is carried out at 100° C. for 10 min. The solvent is removed completely using nitrogen gas at 95° C., and then 200 μL acetonitrile and 500 μL 1 N HCl are added to the reaction vessel. Hydrolysis is performed at 100° C. for 5 min. Pure [$^{18}$F]fluoromisonidazole is obtained by HPLC. The condition of HPLC is as follows; Alltech Econosil C18 column is used, a mixture solution of water:ethanol=95:5 is used at the flow rate of 5 mL/min., and the equipment has a 254 nm UV detector and radioactive detector. In the experiment carried out under the above reaction condition, the attenuation-corrected radiochemical yield is 82.1+1.1% and the radiochemical purity is 98.1+1.5%

<Chemical Equation 6>

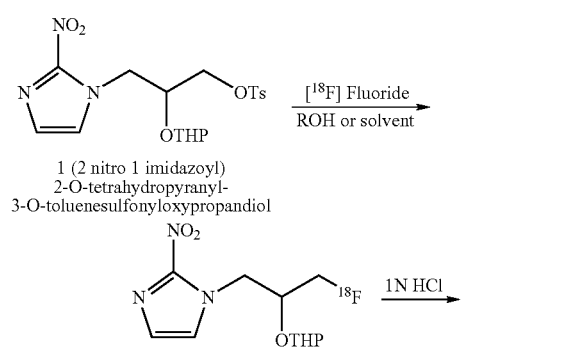

1 (2 nitro 1 imidazoyl)
2-O-tetrahydropyranyl-
3-O-toluenesulfonyloxypropandiol

-continued

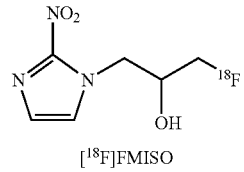

[$^{18}$F]FMISO

Example 19

Preparation of Organofluoro Compound 19

Preparation of [$^{18}$F]fluoroestradiol (FES)

The preparation process of [$^{18}$F]fluoroestradiol is shown in Chemical Equation 7. 10 mCi [$^{18}$F]fluoride is adsorbed on ion exchange resin. The adsorbed [$^{18}$F]fluoride is eluted to a reaction vessel by the mixture solution of cesium carbonate (16 mg in 300 μL water) and Kryptofix 222 (22 mg in 300 μL acetonitrile) or by tetrabutylammonium solution. The [$^{18}$F] fluoride is dried by acetonitrile (500 μL×3). To the solution 3 mg of 3-O-methoxymethyl-16β,17β-epiestriol-0-cyclosulfone is added. After the addition of the mixture solution containing 400 μL of t-butyl alcohol or t-amyl alcohol and 100 μL of acetonitrile to the above reaction mixture, the reaction is carried out at 100° C. for 15 min.

The solvent is completely removed, using nitrogen gas at 95° C., then 200 μL acetonitrile and 50 μL 1 N HCl are added, and hydrolysis is carried out under nitrogen atmosphere at 100° C. for 3 min. while the solvent is removed. The above procedure is carried out three times. The pure [$^{18}$F]fluoroestradiol is obtained by HPLC. The condition of HPLC is as follows;

Nucleosil C18 120-5A C18 column is used, a mixture solution of water:ethanol=40:60 is used at the flow rate of 4 mL/min., and the equipment has a 280 nm UV detector and radioactive detector. In the experiment carried out under the above reaction condition, the attenuation-corrected radiochemical yield is 72.1±1.1% and the radiochemical purity is 98.4±1.2%.

<Chemical Equation 7>

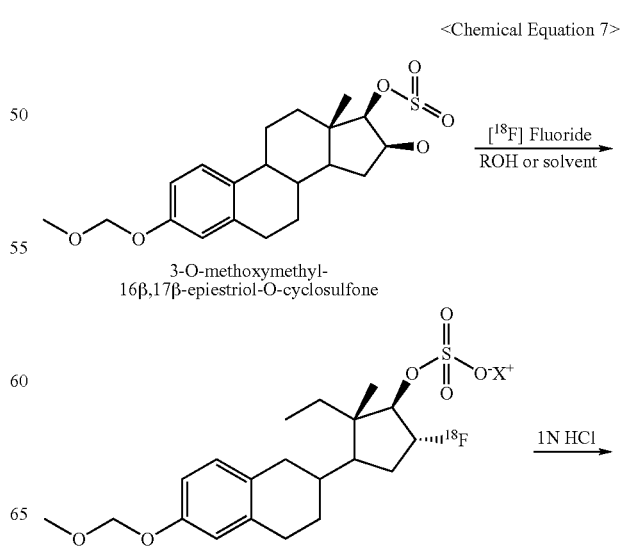

3-O-methoxymethyl-
16β,17β-epiestriol-O-cyclosulfone

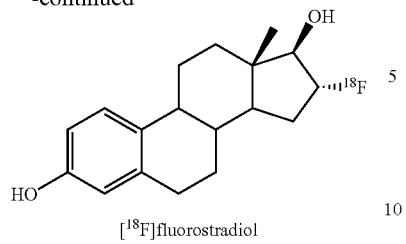

[18F]fluorostradiol

Example 20

Preparation of Organofluoro Compound 20

Automatic Preparation of [18F]fluoroestradiol (FES)

The automatic preparation of [18F]fluoroestradiol is carried out according to the reaction conditions described in Example 19. The apparatus for the automatic preparation is GE TracerLab MX and the operation program is modified for the preparation of [18F]fluoroestradiole. A disposable cassette is used for the preparation and the schematic diagram of the cassette is shown in FIG. 2.

After placing a disposable cartridge for the GE TracerLab MX in the automatic equipment, chemicals are added to vials as follows; 7 mL acetonitrile in 10 mL V1 vial, 3 mg 3-O-methoxymethyl-16β,17β-epiestriol-O-cyclicsulfone (1.5 mL t-butyl alcohol or t-amyl alcohol and 0.5 mL acetonitrile) in 10 mL V2 vial, 3 mL ethanol and the mixture solution of 500 □2N NaOH and 1 mL water in 10 mL V3 vial, 0.63 mL 2N HCl and 6 mL ancetonitrile in V4 vial, and the vials are placed in the disposable cassette.

1.0 Ci of [18F]fluoride is prepared from oxygen-18 labeled water in a cyclotron and then the produced [18F]fluoride is transferred to the GE TracerLab MX automatic equipment by the pressure of helium gas. The transferred [18F]fluoride is adsorbed on the ion exchange cartridge and oxygen-18 is recovered to an oxygen-18 water reservoir. The adsorbed [18F]fluoride is eluted to the reaction vessel by the mixture solution of cesium carbonate (16 mg in 300 □water) and Kryptofix 222 (22 mg in 300 □acetonitrile) or by tetrabutylammonium solution. The eluted [18F]fluoride is completely dried by 1 mL acetonitrile in V1 vial. After the addition of 3-O-methoxymethyl-16β,17β-epiestriol-O-cyclicsulfone in V2 vial to the reaction vessel containing [18F]fluoride, the reaction mixture is treated at 95° C. for 5 min., and then the solvent is removed. Hydrolysis is carried out at 90° C. by adding the mixture solution of 2 mL HCL and acetonitrile in V4 vial to the reaction vessel. This procedure is repeated three times. Solvents are removed after hydrolysis. The mixture solution in V3 vial is added to the reaction vessel to dissolve the reaction mixture. The pure [18F]fluoroestradiol is obtained by HPLC. The condition of HPLC is as follows; Nucleosil C18 120-5A C18 column is used, a mixture solution of water:ethanol=40:60 is used at flow rate of 4 mL/min., and the equipment has a 280 nm UV detector and radioactive detector. In the experiment carried out under the above reaction condition, the attenuation-corrected radiochemical yield is 42.1±5.1% and the radiochemical purity is 98.0±1.1%.

Example 21

Preparation of Organofluoro Compound 21

Preparation of [18F]fluoropropylcarbomethoxytropane (FP-CIT) 1

The preparation process of [18F]fluoropropylcarbo methoxytropane is shown in Chemical Equation 8. 10 mCi of [18F]fluoride is adsorbed on ion exchange resin. The adsorbed [18F]fluoride is eluted to a reaction vessel by the mixture solution of cesium carbonate (16 mg in 300 μL water) and Kryptofix 222 (22 mg in 300 μL acetonitrile) or by tetrabutylammonium solution. The [18F]fluoride is dried by acetonitrile (500 μL×3). 10 mg of 1,3-ditosylpropane is added to this solution. After the addition of the mixture solution containing 500 μL t-butyl alcohol or t-amyl alcohol and 100 μL acetonitrile to the above reaction mixture, the reaction is carried out at 95° C. for 15 min. The solvent is removed using nitrogen gas at 95° C. and then 5 mg of nor-β-CIT dissolved in the mixture solution of 300 D acetonitrile and 500 μL t-butyl alcohol is added. The reaction is carried out at 135° C. for 40 min. The pure [18F]fluoropropylcarbomethoxytropane is obtained by HPLC. The condition of HPLC is as follows; μ-Bondapack C18 column is used, a mixture solution of phosphoric acid:acetonitrile=40:60 is used at the flow rate of 5 mL/min., and the equipment has a 220 nm UV detector and radioactive detector. In the experiment carried out under the above reaction condition, the attenuation-corrected radiochemical yield is 25.3+21% and the radiochemical purity is 97.2+1.3%.

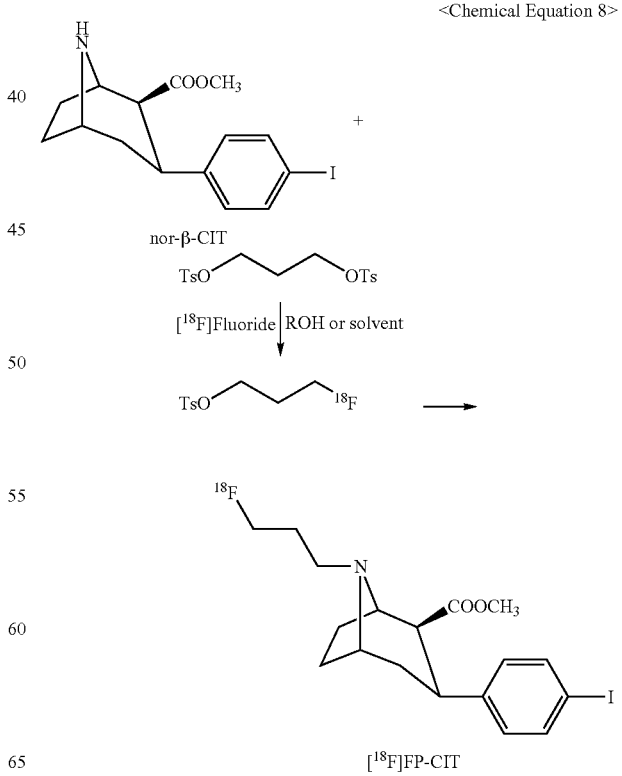

<Chemical Equation 8>

Example 22

Preparation of Organofluoro Compound 22

Preparation of [$^{18}$F]fluoropropylcarbomethoxytropane (FP-CIT) 2

The preparation process of [$^{18}$F]fluoropropylcarbo methoxytropane is shown in Chemical Equation 9. 10 mCi of [$^{18}$F]fluoride is adsorbed on ion exchange resin. The adsorbed [$^{18}$F]Fluoride is eluted to a reaction vessel by the mixture solution of cesium carbonate (16 mg in 300 μL water) and Kryptofix 222 (22 mg in 300 μL acetonitrile). The [$^{18}$F] fluoride is dried by acetonitrile (500 μL×3). After a solution of 5 mg (3-methanesulfonyloxypropyl)-2β-carbomethoxy-3β-(4-iodophenyl)tropane or (3-toluenesulfonyloxypropyl)-2β-carbomethoxy-3β-(4-iodophenyl)tropane is added to the reaction solution, and a mixture solution of 100 μL acetonitrile and 500 μL t-butyl alcohol or t-amyl alcohol is added. The reaction is carried out at 95° C. for 10 min. The solvent is completely removed using nitrogen gas at 95° C. and then 300 μL acetonitrile and 500 μL water are added to reaction vessel. The pure [$^{18}$F]fluoropropylcarbomethoxytropane is obtained by HPLC. The condition of HPLC is as follows; μ-Bondapack C18 column is used, a mixture solution of phosphoric acid: acetonitrile=40:60 is used at the flow rate of 5 mL/min., and the equipment has a 220 nm UV detector and radioactive detector. In the experiment carried out under the above reaction condition, the attenuation-corrected radiochemical yield is 25.3+2.1% and the radiochemical purity is 97.2+1.3%.

<Chemical Equation 9>

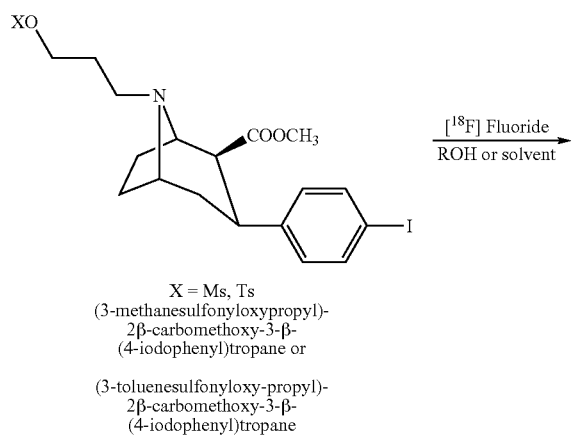

X = Ms, Ts
(3-methanesulfonyloxypropyl)-
2β-carbomethoxy-3-β-
(4-iodophenyl)tropane or (3-toluenesulfonyloxy-propyl)-
2β-carbomethoxy-3-β-
(4-iodophenyl)tropane

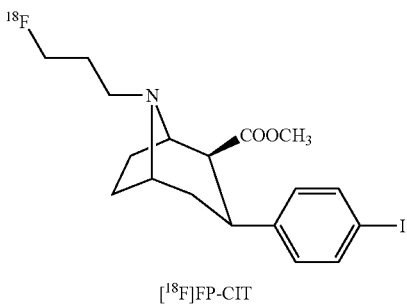

[$^{18}$F]FP-CIT

Example 23

Preparation of Organofluoro Compound 23

Preparation of [$^{18}$F]fluoro-2-dialkylamino-6-acylmalonodinitrile naphthalene (FDDNP)

The preparation process of [$^{18}$F]fluoroDDNP is shown in Chemical Equation 10. 10 mCi of [$^{18}$F]fluoride is adsorbed on ion exchange resin. The adsorbed [$^{18}$F]fluoride is eluted to a reaction vessel by the mixture solution of cesium carbonate (16 mg in 300 μL water) and Kryptofix 222 (22 mg in 300 μL acetonitrile) or by tetrabutylammonium solution. The [$^{18}$F] fluoride is dried by acetonitrile (500 μL×3). 4 mg tosyl precursor of Chemical Equation 10 is added to the solution. After the addition of the mixture solution containing 500 μL t-butyl alcohol or t-amyl alcohol and 100 μL acetonitrile to the above reaction mixture, the reaction is carried out at 95° C. for 10 min. The solvent is removed using nitrogen gas at 95° C. The reaction mixture is dissolved in acetonitrile and the radiochemical yield of the product is measured by radio TLC. In the experiment carried out under the above reaction condition, the attenuation-corrected radiochemical yield is 42.3+4.1% and the radiochemical purity is 97.2+1.3%.

<Chemical Equation 10>

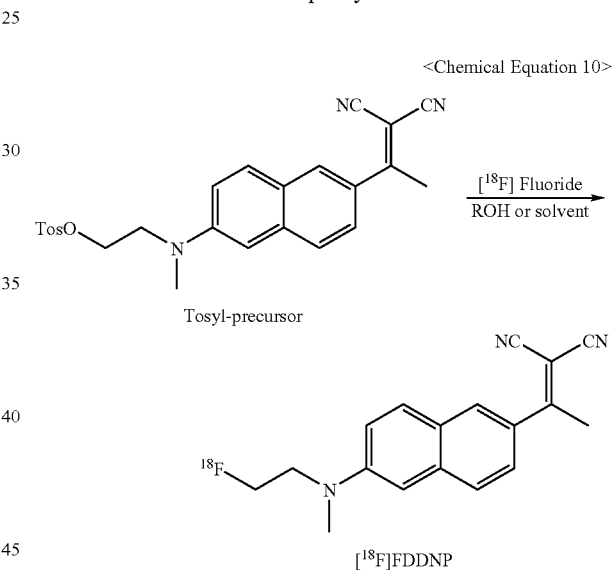

Tosyl-precursor

[$^{18}$F]FDDNP

Example 24

Preparation of Organofluoro Compound 24

Preparation of [$^{18}$F]fluorothymidine (FLT)

Another preparation process of [$^{18}$F]fluorothymidine is shown in Chemical Equation 11. 10 mCi of [$^{18}$F]fluoride is adsorbed on ion exchange resin. The adsorbed [$^{18}$F]fluoride is eluted a to reaction vessel by the mixture solution of cesium carbonate (16 mg in 300 μL water) and Kryptofix 222 (22 mg in 300 μL acetonitrile) or by tetrabuty-lammonium solution. The [$^{18}$F]fluoride is dried by acetonitrile (500 μL×3). 10~40 mg of 3-N-t-butoxycarbonyl-(5'-O-(4,4'-dimethoxytriphenylmethyl)-2-deoxy-3'-O-(4-nitrobenzensulfonyl)-β-D-threo-pentofuranosyl)thymine or 3-N-t-butoxycarbonyl-(5'-O-(triphenylmethyl)-2-deoxy-3'-O-(4-nitrobenzensulfonyl)-β-D-threo-pentofuranosyl)thymine is added to the solution, and then the mixture solution of 100 μL acetonitrile and 500

μL t-butyl alcohol or t-amyl alcohol is added. The reaction is carried out at 100~150° C. for 10 min. The solvent is removed using nitrogen gas at 95° C., and then 200 μL acetonitrile and 500 μL 1 N HCl are added. Hydrolysis reaction is carried out at 100° C. for 5 min. Pure [$^{18}$F]fluorothymidine is obtained by HPLC. The condition of HPLC is as follows; Alltech Econosil C18 column is used, a mixture solution of water:ethanol=90:10 is used at the flow rate of 5 mL/min., and the equipment has a 267 nm UV detector and radioactive detector. In the experiment carried out under the above reaction condition, the attenuation-corrected radiochemical yield is 85.6+3.1% and the radiochemical purity is 98.5+1.2%.

<Chemical Equation 11>

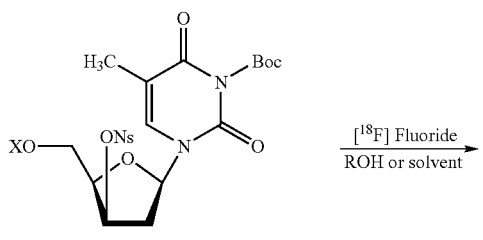

X-Ir or DM'r
3-N-t-butoxycarbonyl-(5'-O-triphenylmethyl)-2-deoxy-3'-O-(4 nitrobenzensulfonyl)-β-D-threo-pentofuranosyl)thymine or
3-N-t-butoxycarbonyl-(5'-O-(4,4'-dimethoxy triphenylmethyl)-2-deoxy-3'-O-(4-nitrobenzensulfonyl)-β-D-threo-pentofuranosyl)thymine

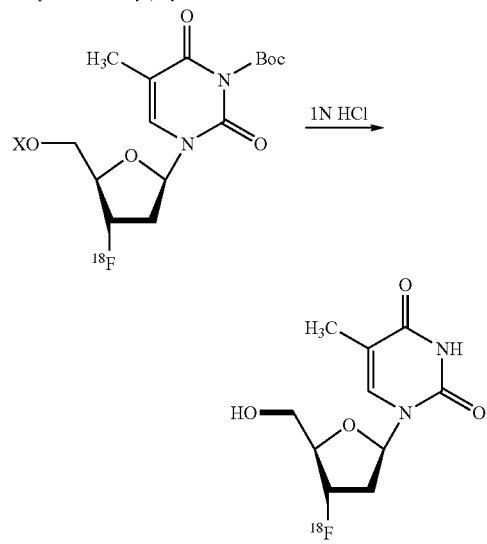

Example 25

Preparation of Organofluoro Compound 25

Preparation of [$^{18}$F]fluorocholine (FCholine)

Another preparation process of [$^{18}$F]fluorocholine is shown in Chemical Equation 12. 10 mCi of [$^{18}$F]fluoride is adsorbed on ion exchange resin. The adsorbed [$^{18}$F]fluoride is eluted to a reaction vessel by the mixture solution of cesium carbonate (16 mg in 300 μL water) and Kryptofix 222 (22 mg in 300 μL acetonitrile) or by tetrabuty-lammonium solution. The [$^{18}$F]fluoride is dried by acetonitrile (500 μL×3). 10 mg of 1,1-di-p-toluenesulfonyloxymethane is added to the solution and then the mixture solution containing 500 μL t-butyl alcohol or t-amyl alcohol and 100 μL acetonitrile are added. The reaction is carried out at 100-150° C. for 10 min. After the reaction is finished, N,N-dimethylaminoethanol is added for alkylation. Pure [$^{18}$F]fluorocholine is obtained by HPLC. In the experiment carried out under the above reaction condition, the attenuation-corrected radiochemical yield is 75.7±3.1% and the radiochemical purity is 97.5+1.2%.

<Chemical Equation 12>

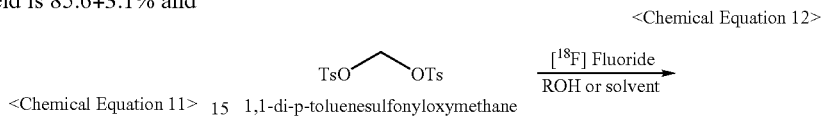

Example 26

Preparation of Organofluoro Compound 26

Preparation of [$^{18}$F]fluoroethylcholine (FECholine)

Another preparation process of [$^{18}$F]fluoroethylcholine is shown in Chemical Equation 13. 10 mCi of [$^{18}$F]fluoride is adsorbed on ion exchange resin. The adsorbed [$^{18}$F]fluoride is eluted to a reaction vessel by the mixture solution of cesium carbonate (16 mg in 300 μL water) and Kryptofix 222 (22 mg in 300 μL acetonitrile) or by tetrabuty-lammonium solution. The [$^{18}$F]fluoride is dried by acetonitrile (500 μL×3). 10 mg of 1,2-di-p-toluenesulfonyloxymethane is added to the solution, and then the mixture solution containing 500 μL t-butyl alcohol or t-amyl alcohol and 100 μL acetonitrile is added. The reaction is carried out at 100-150° C. for 10 min. After the reaction is finished, N,N-dimethylaminoethane is added for alkylation. Pure [$^{18}$F]fluoroethylcholine is obtained by HPLC. In the experiment carried out under the above reaction condition, the attenuation-corrected radiochemical yield is 67.7+8.1% and the radiochemical purity is 98.2+2.3%.

<Chemical Equation 13>

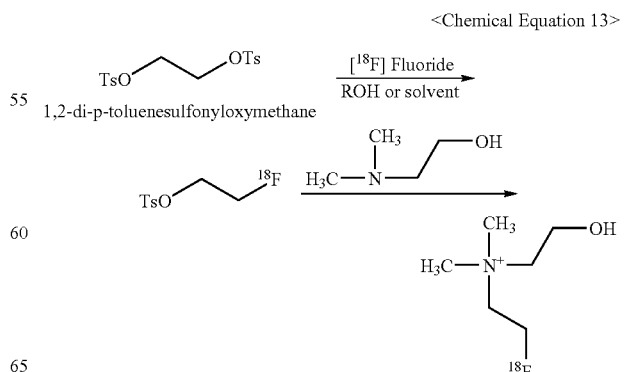

Example 27

Preparation of Organofluoro Compound 27

Preparation of [$^{18}$F]fluoropropylcholine (FPCholine)

The preparation process of [$^{18}$F]fluoropropylcholine is shown in Chemical Equation 14. 10 mCi of [$^{18}$F]fluoride is adsorbed on ion exchange resin. The adsorbed [$^{18}$F]Fluoride is eluted to a reaction vessel by the mixture solution of cesium carbonate (16 mg in 300 μL water) and Kryptofix 222 (22 mg in 300 μL acetonitrile) or by tetrabuty-lammonium solution. The [$^{18}$F]fluoride is dried by acetonitrile (500 μL×3). 10 mg of 1,3-di-p-toluenesulfonyloxypropane is added to the solution, and then the mixture solution containing 500 μL t-butyl alcohol or t-amyl alcohol and 100 μL acetonitrile is added. The reaction is carried out at 100-150° C. for 10 min. After the reaction is finished, N,N-dimethylaminoethanol is added for alkylation. Pure [$^{18}$F]fluoropropylcholine is obtained by HPLC. In the experiment carried out under the above reaction condition, the attenuation-corrected radiochemical yield is 72.4+6.1% and the radiochemical purity is 98.1+1.3%.

<Chemical Equation 14>

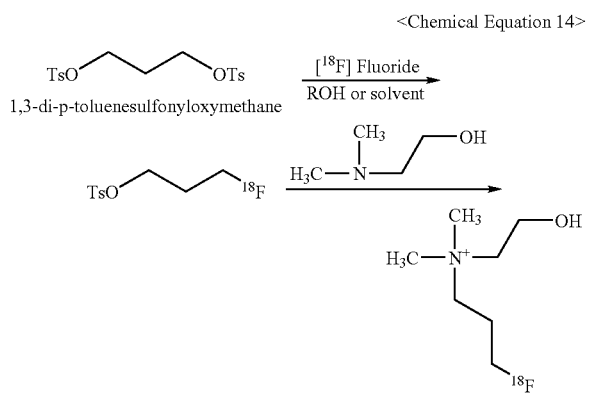

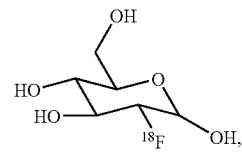

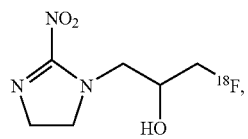

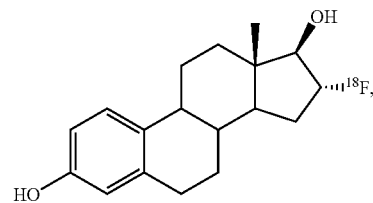

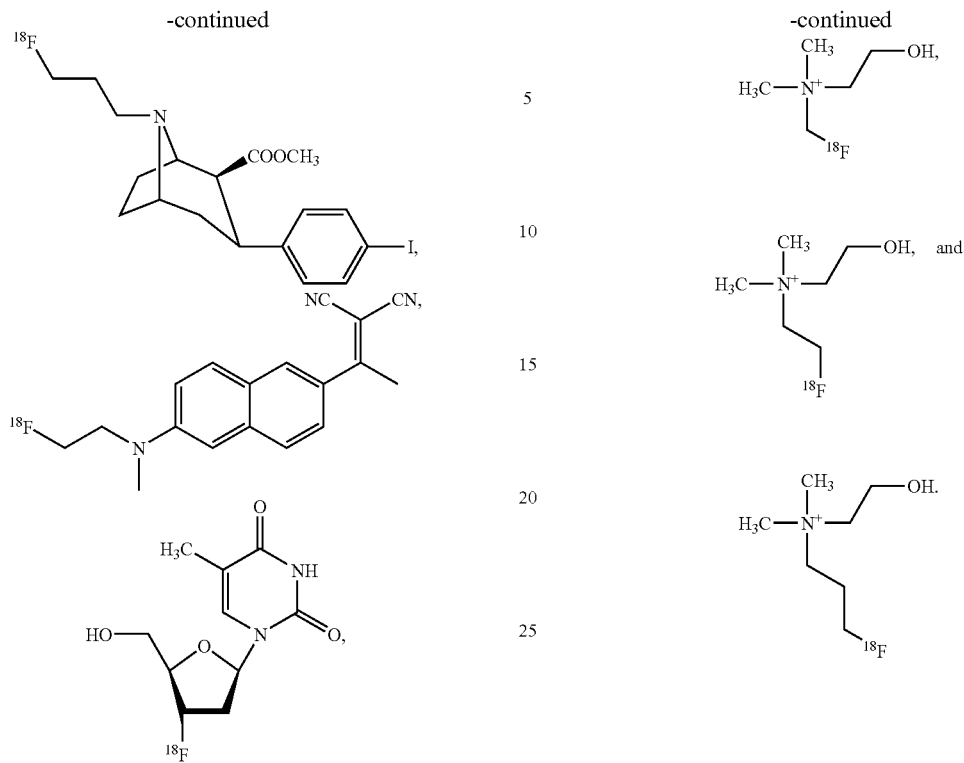

The invention claimed is:

1. A method for the preparation of primary or secondary [$^{18}$F]organofluoro compounds consisting essentially of reacting a [$^{18}$F]fluorine salt with a primary or secondary alkyl halide or a primary or secondary alkyl sulfonate in the presence of an alcohol of Chemical Formula 1 as solvent, <Chemical Formula 1>

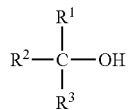

wherein R$^1$, R$^2$ and R$^3$ are hydrogen or C$_{1-3}$ alkyl group.

2. The method of claim 1, wherein R$^1$ is methyl or ethyl; R$^2$ is methyl or ethyl; and R$^3$ is methyl or ethyl.

3. The method of claim 1, wherein the alcohol of Chemical Formula 1 is selected from the group consisting of primary alcohols of methanol, ethanol, and n-propanol; secondary alcohols of isopropanol, isobutanol, and 3-pentanol; and tertiary alcohols of t-butanol, t-amyl alcohol, 2,3-dimethyl-2-butanol, 2-(trifluoromethyl)-2-propanol, 3-methyl-3-pentanol, 3-ethyl-3-pentanol, 2-methyl-2-pentanol, 2,3-dimethyl-3-pentanol, 2-cyclopropyl-2-propanol, 2-cyclopropyl-2-butanol, 2-cyclopropyl-3-methyl-2-butanol.

4. The method of claim 1, wherein the alcohol of Chemical Formula 1 is t-butanol or t-amyl alcohol.

5. The method of claim 1, wherein the [$^{18}$F]fluorine salt is cesiumfluoride or tetraalkylammonium fluoride, and the alcohol is selected from the group consisting of t-butanol, t-amyl alcohol, 2,3-dimethyl-2-butanol and 2-(trifluoromethyl)-2-propanol.

6. The method of claim 1, wherein the [$^{18}$F]fluorine salt is selected from the group consisting of alkali metal fluorides, alkaline earth metal fluorides and ammonium fluoride, wherein, the alkali metal is selected from the group consisting of lithium, sodium, potassium, rubidium, and cesium; and the alkaline earth metal is selected from the group consisting of magnesium, calcium, strontium, and barium.

7. The method of claim 6, wherein the ammonium fluoride is selected from the group consisting of quaternary ammonium fluorides including tetrabutylammonium fluoride and benzyltrimethylammonium fluoride, tertiary ammonium fluorides including triethylammonium fluoride and tributylammonium fluoride, secondary ammonium fluorides including dibutylammonium fluoride and dihexylammonium fluoride, and primary ammonium fluorides including butylammonium fluoride and hexylammonium fluoride.

8. The method of claim 1, wherein the [$^{18}$F]fluorine salt is selected from the group consisting of cesium fluoride and tetraalkylammonium fluoride.

9. The method of claim 8, wherein the cesium fluoride or the tetraalkylammonium fluoride is adsorbed on a support selected from the group consisting of Celite, Molecular Sieve, alumina, and silica gel.

10. The method of claim 1, wherein the amount of the [$^{18}$F]fluorine salt is 1.0~10 equivalents of the [$^{18}$F]containing alkyl halide or alkyl sulfonate; wherein 1 pg~100 ng of [$^{18}$F] fluoride is used per 1 mg of the alkyl halide or alkyl sulfonate.

11. The method of claim 1, wherein the [$^{18}$F]organofluoro compound is selected from the group consisting of: